United States Patent [19]

Brown et al.

[11] Patent Number: 4,812,067

[45] Date of Patent: Mar. 14, 1989

[54] DISPOSABLE APPLICATOR PACKAGE

[76] Inventors: James B. Brown, 690 Bedford Rd., Armonk, N.Y. 10504; Jack W. Kaufman, 357 Frankel Blvd., Merrick, N.Y. 11566

[21] Appl. No.: 120,345

[22] Filed: Nov. 13, 1987

[51] Int. Cl.$^4$ .................. B65D 35/00; A47L 13/17
[52] U.S. Cl. .................. 401/132; 401/133; 401/196; 604/3
[58] Field of Search ........... 401/132, 133, 196; 604/3, 416; 222/92, 94, 107, 541; 15/244.1

[56] References Cited

U.S. PATENT DOCUMENTS

| 3,315,801 | 4/1967 | Lowry | 222/94 X |
| 4,140,409 | 2/1979 | DeVries | 401/132 |
| 4,236,652 | 12/1980 | Beguhn | 222/92 |
| 4,331,264 | 5/1982 | Staar | 222/94 |
| 4,430,013 | 2/1984 | Kaufman | 401/132 |

FOREIGN PATENT DOCUMENTS

| 373227 | 4/1923 | Fed. Rep. of Germany | 604/416 |
| 2751078 | 5/1979 | Fed. Rep. of Germany | 222/107 |

Primary Examiner—Richard J. Apley
Assistant Examiner—Franklin L. Gubernick
Attorney, Agent, or Firm—Seymour G. Bekelnitzky

[57] ABSTRACT

An applicator package for the application of flowable materials to surfaces, comprising: an applicator pad; a backing member, one surface of which is in adhesive contact with the pad, comprising a first, flexible sheet; a second member, in contact with the other surface of the backing member, comprising a formed semi-rigid sheet having at least one recess adjacent the pad; at least one cavity, or reservoir for flowable materials distally spaced from the recess; a peripheral groove in fluid connection with the recess and spaced from the distal and side edges of the member; co-planar separations, between the cavity and the groove and recess, in contact with the backing member the backing member being sealed to the second member at the periphery thereof and at the separations between the cavity, groove and recess; and an opening adjacent to and between the pad and the recess to permit the flow of the flowable materials therethrough into the pad and therethrough to the desired surfaces.

25 Claims, 5 Drawing Sheets

DISPOSABLE APPLICATOR PACKAGE

FIELD OF THE INVENTION

This invention relates to disposable applicator packages, such as swabs and the like, for the application of flowable materials, such as medications and antiseptics, to surfaces. More particularly, it relates to an applicator package comprising an applicator pad adherent to one side of a backing member comprising a flexible, flat sheet, having a slit or weakened portion therein adjacent to said applicator pad. Said package further comprises a second member in sealable contact with the other side of said backing member said second member comprising a semi-rigid formed flat sheet comprising, at its distal ends, and spaced from the edges of said sheet two cavities, or reservoirs, for the containment of said flowable materials or precursors thereof; two recesses for containment of said flowable materials or the precursors thereof after explusion from said reservoirs and prior to transfer to said applicator pad disposed between said cavities; a peripheral groove, spaced from the edges of said second member and separated from said reservoirs, in fluid connection with said recesses; a second separation between said reservoirs and recesses said separations being co-planar and in contact with said backing member; a separation between said recesses spaced below the plane of said separations between said reservoirs and said groove and said recesses to permit fluid connection between said recesses over said connection, said backing member and second member being sealed to each other peripherally and at the separations between said reservoirs and said grooves to prevent premature leakage or diffusion from said reservoirs.

BACKGROUND OF THE INVENTION

In the prior art, U.S. Pat. No. 4,430,013 to Kaufman, there is described an applicator package, such as disposable swabs and like, comprising an applicator pad having a backing member adjacent and adherent, at one surface thereof, to said pad said backing member having a transverse slit or weakened portion therethrough adjacent to said applicator pad; and a formed second member adjacent and adherent to the other side of said backing member comprising a pair of reservoirs for the containment of flowable materials, to be dispersed through said pad, each having necked down portions leading to fanned out proximal portions adjacent said slit or weakened portion wherein said flowable materials are transferred to said pad and therethrough to a desired surface or otherwise, as desired, upon the opening of said slit or weakened portion and compression of said reservoirs by moving the distal ends of said package towards each other on the side opposite said pad. Said members are caused to adhere to each other, peripherally, by means of heat sealing or adhesives.

The above invention suffers from the disadvantage that, upon compression of said reservoirs the contents thereof may, instead of flowing through the slit or weakened portion into said pad, burst through said seals and be expelled from the package around its edges with the concomitant result that it may flow over the operator's digits, or other body parts, clothing and the surroundings as well as being depleted for application to said surface.

Furthermore, if the materials contained in the reservoirs must be separated from each other because they will interact to form the material to be applied to the surface said separation can not be effected with the above invention and consequently the interaction of the contained substances will occur in an uncontrolled and non-uniform manner.

It has now been found that said disadvantages may be overcome by the package taught in accordance with the instant invention.

SUMMARY

It is an object of this invention to provide an applicator package, for the application of flowable materials to a surface, comprising an applicator pad and a reservoir for the containment of said flowable materials wherein said reservoir and pad are so disposed that said flowable materials can not reach said pad until dispensation thereof is desired.

It is a further object of this invention to provide an applicator package, for the application of flowable materials to a surface, comprising an applicator pad and a reservoir for the containment of said flowable materials wherein said applicator pad is adjacent and adherent to an approximately central portion of a backing member said backing member comprising a slit or weakened portion adjacent said pad.

According to another object of this invention there is provided an applicator package, for the application of flowable materials to a surface, comprising an applicator pad adjacent and adherent to an approximately central portion of the first surface of a backing member further comprising a slit or weakened portion adjacent said pad; a second member comprising a cavity distally separated from the center of said second member, said cavity comprising a reservoir for the containment of said flowable materials, said second member being in sealable contact with said backing member.

Another object of this invention is to provide an applicator package, for the application of flowable materials to a surface, comprising an applicator pad adjacent and adherent to an approximately central portion of the first surface of a backing member further comprising a slit or weakened portion adjacent said pad; a second member comprising a cavity distally separated from the center of said second member, said cavity comprising a reservoir for the containment of said flowable materials, said second member being in sealable contact with said backing member and further comprising, between said reservoir and the portion of said second member adjacent said slit or weakened portion a recess, adjacent said slit or weakened portion, to receive said flowable materials prior to their absorption by said pad.

Another object of this invention is to provide an applicator package, for the application of flowable materials to a surface, comprising an applicator pad adjacent and adherent to an approximately central portion of the first surface of a backing member further comprising a slit or weakened portion adjacent said pad; a second member comprising a cavity distally separated from the center of said second member, said cavity comprising a reservoir for the containment of said flowable materials, said second member being in sealable contact with said backing member and further comprising, between said reservoir and the portion of said second member adjacent said slit or weakened portion a recess, adjacent said slit or weakened portion, to receive said flowable material prior to their absorption by said pad wherein said reservoir and said recess are separated from each other by portions of said second member disposed therebetween in sealable contact with said backing member.

Another object of this invention is to provide an applicator package, for the application of flowable materials to a surface, comprising an applicator pad adjacent and adherent to an approximately central portion of the first surface of a backing member further comprising a slit or weakened portion adjacent said pad; a second member comprising a cavity distally separated from the center of said second member, said cavity comprising a reservoir for the containment of said flowable materials, said second member being in sealable contact with said backing member and further comprising, between said reservoir and the portion of said second member adjacent said slit or weakened portion a recess, adjacent said slit or weakened portion, to receive said flowable materials prior to their absorption by said pad wherein said reservoir and said recess are separated from each other by portions of said second member disposed therebetween in sealable contact with said backing member wherein said reservoir and said recess are separated from each other by portions of said second member disposed therebetween in sealable contact with said backing member wherein said second member further comprises a peripheral groove in fluid connection with said cavity and separated from said reservoir.

According to another object of this invention there is provided an applicator package, for the application of flowable materials to a surface, comprising an applicator pad adjacent and adherent to an approximately central portion of the first surface of a backing member further comprising a slit or weakened portion adjacent said pad; a second member comprising a cavity distally separated from the center of said second member, said cavity comprising a reservoir for the containment of said flowable materials, said second member being in sealable contact with said backing member and further comprising, between said reservoir and the portion of said second member, adjacent said slit or weakened portion, a recess, adjacent said slit or weakened portion, to receive said flowable materials prior to their absorption by said pad wherein said reservoir and said recess are separated from each other by portions of said second member disposed therebetween in sealable contact with said backing member wherein said backing member further comprises a peripheral groove in fluid connection with said cavity and separated from said reservoirs with said backing member, comprising, between said reservoirs at least two recesses, adjacent said slit or weakened portion, to receive said flowable materials prior to their absorption by said pad wherein said reservoirs and said recesses are separated from each other by portions of said second member disposed therebetween in sealable contact with said backing member wherein said second member further comprises a peripheral groove in fluid connection with said cavities and separated from said reservoirs wherein said recesses are separated from each other by a separation spaced below the surface plane of the second member and the plane of the separations between said groove and said reservoirs.

Yet another object of this invention is to provide an applicator package, for the application of flowable materials to a surface, said flowable materials being formed, just prior to application to the surface, by the interaction of at least two reactive materials, comprising an applicator pad adjacent and adherent to an approximately central portion of the first surface of a backing member further comprising a slit or weakened portion adjacent said pad; a second member comprising at least two cavities diatally separated from the center of said second member, said cavities comprising reservoirs for the containment of said active materials, said second member being in sealable contact with said backing member and further comprising, between said reservoirs and the portion of said second member, adjacent said slit or weakened portion, a recess, adjacent said slit or weakened portion, to receive said active materials and where they may interact to form the flowable materials prior to their absorption by said pad wherein said reservoirs and said recess are separated from each other by portions of said second member disposed therebetween in sealable contact with said backing member wherein said backing member further comprises a peripheral groove in fluid connection with said recess and separated from said reservoirs and the side and distal edges of said second member.

A further object of this invention is to provide an applicator package, for the application of flowable materials to a surface, said flowable materials being formed, just prior to application to the surface, by the interaction of at least two reactive materials, comprising an applicator pad adjacent and adherent to an approximately central portion of the first surface of a backing member further comprising a slit or weakened portion adjacent said pad; a second member comprising at least two cavities distally separated from the center of said second member, said cavities comprising reservoirs for the containment of said active materials, said second member being in sealable contact with said backing member and further comprising, between said reservoirs and the portion of said second member, adjacent said slit or weakened portion, two recesses, adjacent said slit or weakened portion, to receive said active materials and where they may interact to form the flowable materials prior to their absorption by said pad wherein said reservoirs and said recesses are separated from each other by portions of said second member disposed therebetween in sealable contact with said backing member wherein said backing member further comprises a peripheral groove in fluid connection with said recesses and separated from said reservoirs and the side and distal edges of said second member.

Yet another object of the invention is to provide a disposable applicator package as described above wherein said second member comprises a single cavity and a recess comprising tapered side walls the proximal end of the bottom wall of which is approximately parallel to, and spaced vertically from the absorbent pad which is situated adjacent to the proximal ends of said members and whose ends are bent backwards to adhesively contact the upper and lower sides of the backing and second members, respectively.

Another object of this invention is to provide a method for applying flowable materials to a surface, from an applicator package, which comprises the steps of forcing said flowable materials from a reservoir into a recess adjacent an applicator pad through a slit or weakened portion in a backing member, disposed between said recess and said slit or weakened portion, by application of force to the bottom of reservoir; bending the distal ends of the applicator package backwards about said applicator pad whereby the slit or weakened portion is opened, to permit the flowable materials to enter the pad, and said recess is compressed to force the flowable materials into said pad; and thence using said bent backward distal ends of said applicator package as handles to support said pad during said application wherein said applicator package, comprising an applicator pad adjacent and adherent to an approximately central portion of the first surface of a backing member further comprising a slit or weakened portion adjacent said pad; a second member comprising a cavity distally separated from the center of said second member, said cavity comprising a reservoir for the containment of said flowable materials, said second member being in sealable contact with said backing member and further comprising, between said reservoir and the portion of said second member, adjacent said slit or weakened portion, a recess, adjacent said slit or weakened portion, to receive said flowable materials prior to their absorption to said pad wherein said reservoir and said recess are separated from each other by portions of said second member disposed therebetween in sealable contact with said backing member wherein said backing member further comprises a peripheral groove in fluid connection with said cavity and separated from said reservoirs with said backing member, comprising, between said reservoirs at least two recesses, adjacent said slit or weakened portion, to receive said flowable materials prior to their absorption by said pad wherein said reservoirs and said recesses are separated from each other by portions of said second member disposed therebetween in sealable contact with said backing memer wherein said second member further comprises a peripheral groove in fluid connection with said cavities and separated from said reservoirs wherein said recesses are separated from each other by a separation spaced below the surface plane of the second member and the plane of the separations between said groove and said reservoirs.

Yet another object of this invention is to provide a method for applying flowable materials to a surface, from an applicator package, said flowable materials material being formed, just prior to application, by the interaction of at least two active materials, which comprises the steps of forcing said flowable materials from at least two reservoirs into two recess, where they are permitted to interact to form said flowable materials, adjacent an applicator pad through a slit or weakened portion in a backing member, by application of force to the bottom of said reservoirs; bending the distal ends of the applicator package backwards about said applicator pad whereby the slit or weakened portion is opened, to permit the flowable materials to enter the pad, and said recesses are compressed to force the flowable materials into said pad; and thence using said bent backward distal ends of said applicator package as handles to support said pad during said application wherein said applicator package an applicator pad adjacent and adherent to an approximately central portion of the first surface of a backing member further comprising a slit or weakened portion adjacent said pad; a second member comprising a cavity distally separated from the center of said second member, said cavity comprising a reservoir for the containment of said flowable materials, said second member being in sealable contact with said backing member and further comprising, between said reservoir and the portion of said second member, adjacent said slit or weakened portion, a recess, adjacent said slit or weakened portion, to receive said flowable materials prior to their absorption by said pad wherein said reservoir and said recess are separated from each other by portions of said second member disposed therebetween in sealable contact with said backing member wherein said backing member further comprises a peripheral groove in fluid connection with said cavity and separated from said reservoirs with said backing member, comprising, between said reservoirs at least two recesses, adjacent said slit or weakened portion, to receive said flowable materials prior to their absorption by said pad wherein said reservoirs and said recesses are separated from each other by portions of said second member disposed therebetween in sealable contact with said backing member wherein said second member further comprises a peripheral groove in fluid connection with said cavities and separated from said reservoirs wherein said recesses are separated from each other by a separation spaced below the surface plane of the second member and the plane of the separations between said groove and said reservoirs.

Yet another object of this invention is to provide a method for applying flowable materials to a surface which comprises the steps of bending the distal ends of an applicator package for the application of flowable materials to a surface, said flowable materials material being formed, just prior to application, by the interaction of at least two active materials, said applicator package comprising an applicator pad and a backing member adherent thereto wherein said backing member further comprises a slit or weakened portion adjacent said pad and a second member, in sealable contact with said backing member, comprising at least two recesses comprising reservoir at the distal portions thereof, for the containment and separation of said active materials, a peripheral groove spaced from the edges of said second member and at least one recess, in fluid connection with said groove and adjacent said slit or weakened portion, wherein the active materials contained within said reservoir may interact and be transferred to said pad.

Yet another object of this invention is to provide a method for applying flowable materials to a surface which comprises the steps of bending an appicator package for the application of flowable materials to a surface, said flowable materials material being formed, just prior to application, by the interaction of at least two active materials, said applicator package comprising an applicator pad and a backing member adherent thereto wherein said backing member further comprises a slit or weakened portion adjacent said pad and a second member, in sealable contact with said backing member, comprising at least two recesses comprising reservoir at the distal portions thereof, for the containment and separation of said active materials, a peripheral groove spaced from the edges of said second member and at least two cavities, separated from each other by a separation spaced from the plane of the separations between said reservoir and said groove, and in fluid connection with each other by means of said groove and over said separation therebetween in fluid adjacent said slit or weakened portion, wherein the active materials transferred from said reservoir may interact and be transferred to said pad.

Other embodiments or modifications may be suggested to those having the teachings herein and are a part of the invention to the extent they fall within the scope and spirit of the appended claims.

DESCRIPTION OF THE DRAWINGS

FIG. 2 is an exploded vertical sectional view of said package taken along line 1—1 of FIG. 1a.

DETAILED DESCRIPTION OF A PREFERRED EMBODIMENT

In accordance with this invention there is provided an applicator package, for the application of flowable materials, which may be present in the package in their final form or which may be formed, from the contents of the package, prior to their application to said surfaces.

Said package comprises an absorbent applicator pad disposed at or about the central portion of, and adherent to a backing member having a slit or weakened portion therein adjacent said pad, and a second member comprising a formed, flat semi-rigid sheet in contact with said backing member comprising at least one cavity, or reservoir, for the containment of said flowable materials if said materials are in the final form for application or at least two reservoirs if they contain precursors to said flowable materials said reservoirs being spaced distally from the portion of said second member adjacent said slit or weakened portion and at least one recess, to accept said compositions prior to application thereof, adjacent said slit or weakened portion and in fluid connection therewith, separations between said reservoirs and said recesses in contact with the lower surface of said backing member; a peripheral groove, in fluid connection with said recesses, spaced from said cavities and the distal and side edges of said second member.

Referring to the accompanying drawings, wherein similar reference numbers designate similar parts throughout, 1 indicates an applicator package, for the application of flowable materials to surfaces, comprising a porous applicator pad 11 adjacent and adherent to one side of a backing member 2 comprising a flat, flexible first sheet 10 further comprising a longitudinal slit or weakened portion 12 in the portion thereof adjacent said pad 11.

The applicator package further comprises a second member 3 comprising a flat, formed sheet 20, comprising, at its distal ends, two cavities 27 to act as reservoirs, for the flowable materials, to be applied to said surfaces, or to precursors for said materials; two recesses 28, between said reservoirs 27 to receive said flowable materials or the precursors therefor; and peripherally a groove 23 separated from said reservoirs 27 and the distal and side edges thereof by separations 24 and 25, respectively, and from the distal and side edges of said second member 3 by separations 21 and 22, respectively, said separations being co-planar and in contact with the under surface 14 of said backing member 2, said reservoirs 27 being separated from said recesses 28 by separations 26; and said recesses being separated from each other by a separation 29, spaced below the plane of the above separations, over which fluid connection between said recesses may be attained, said backing member 2 being in contact with said second member 3 at its edges and the co-planar separations and in fluid connection with said recesses 28 through the slit or weakened portion 12.

The first 2 & second 3 members are sealed to each other peripherally and at the separations 24 and 25 between said reservoirs 27 and the groove 23 and the separations 26 between said reservoirs 27 and said recesses 28 by heat sealing or other means. If the sealing is to be effected by means of an adhesive it is to be understood that said adhesives are to be chosen from such as are not reactive with said flowable or active materials and will not permit premature leakage or diffusion of such materials therethrough to the groove 23 or recesses 28.

In the practice of using the invention pressure, e.g., from a thumb, is applied to the bottom wall 30 of one or both of said reservoirs 27 whereby the materials contained therein are forced outward breaking the seals between said reservoirs 27 and the groove 23 and the recesses 28 whereby the said materials are caused to flow to the recesses 28 and not through the contact between said backing member and said second member 3.

The flowable materials contained within said recesses 28 are then transferred to said pad 11 through said slit or weakened portion 12 which is opened by bending the distal ends of the package backwards by application of pressure to the distal edges of the upper surface 13 of the backing member 2 and applying pressure to the bottom walls 31 of said recesses.

In the event that the material to be applied to the surfaces is not the contents of the reservoirs 27 but rather is formed by interaction of said contents, said contents, after entering said recesses 28, are swirled therebetween, over said separation 29, until the desired extent of reaction has occurred and the final product is then transferred from the recesses 28 to said pad 11 as described above.

The bent back distal ends of the package may then function as handles to form, together with the bent back pad 11, a swab or the like, for applying the flowable materials to the surface. Alternatively, after transfer of said flowable materials to the pad 11 said members may be separated, as by peeling, and the distal ends of the backing member 2 bent backwards to form such handles.

Figures 1A, 1B:
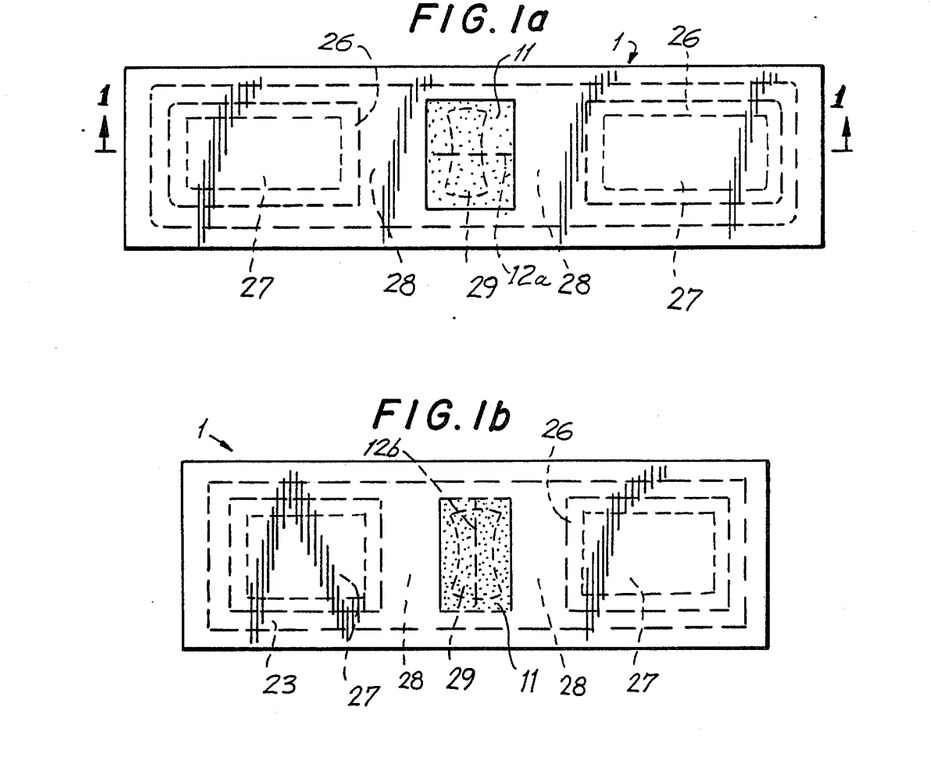
FIG. 1a is a top perspective view of an applicator package according to the instant invention.
FIG. 1b is a top perspective view of another aspect of the above package.
Figure 2:
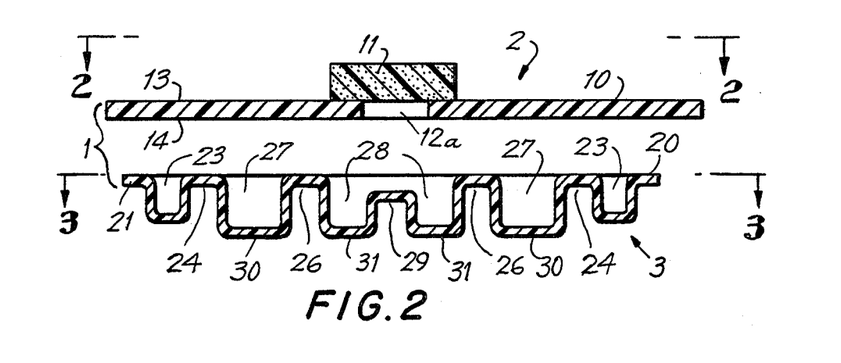
Figure 3:
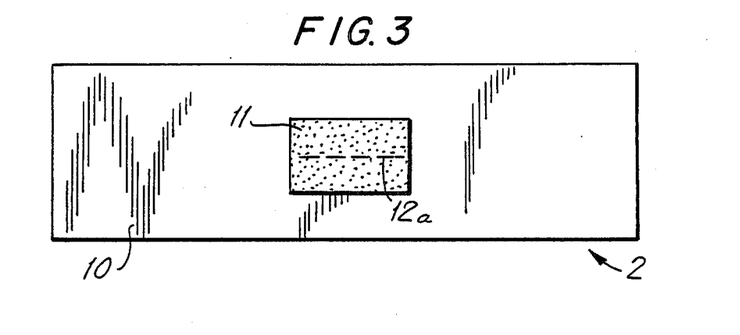
FIG. 3 is a top view of the backing member and applicator pad of said package taken along line 2—2 of FIG. 2 in the direction indicated.
Figure 4:
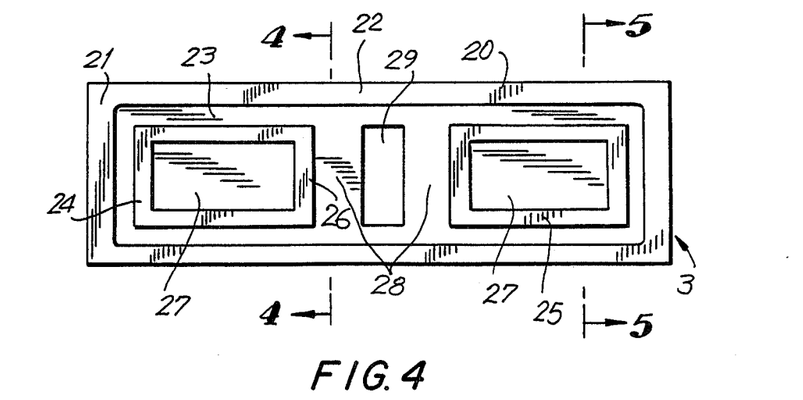
FIG. 4 is a top view of the second member of said package taken along line 3—3 of FIG. 2 in the direction indicated.
Figure 5:
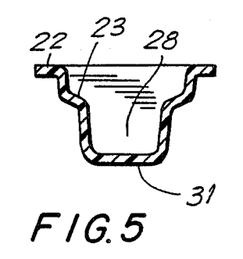
FIG. 5 is a vertical sectional view of said second member taken along line 4—4 of FIG. 4.
Figure 6:
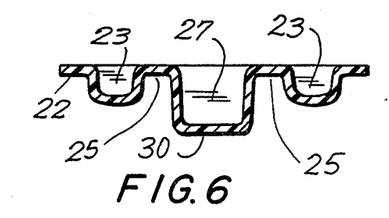
FIG. 6 is a vertical sectional view of said second member taken along line 5—5 of FIG. 4.
Figure 7:
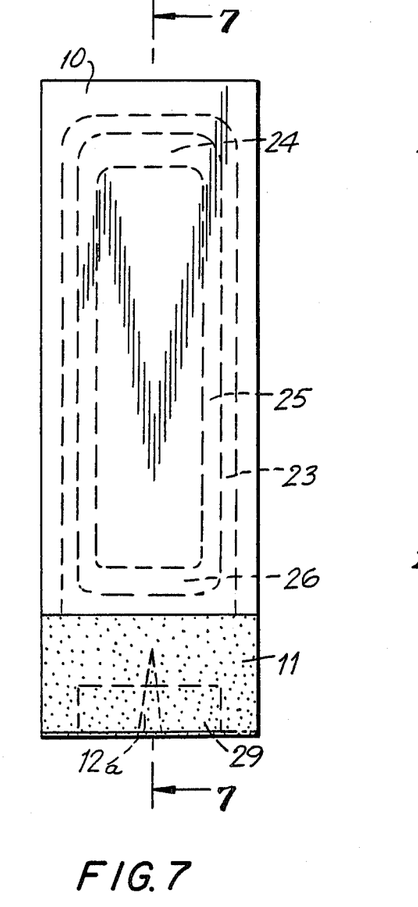
FIG. 7 is a front view of the applicator package with the distal ends bent backwards towards each other.
Figure 8:
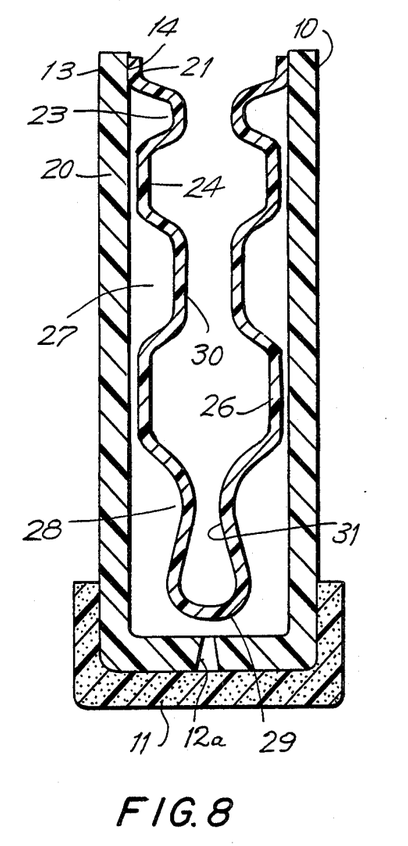
FIG. 8 is a side view of the applicator package taken along line 7—7 of FIG. 7.

In one embodiment wherein the flowable materials in said reservoirs 27 are already in the desired form for application to the surface, the contents of both reservoirs 27 being the same or different, the applicator may be used for at least two applications by first compressing only one of said reservoirs 27 and at a later time the other one. In this embodiment, of course, the members are not separated from each other but, rather the distal ends of the applicator package are bend backwards, towards each other, to form a handle, as shown in FIGS. 7 and 8, for the swab which is then used to apply said flowable materials to said surface.

In the alternative when it is desired to utilize the contents of both reservoirs 27 at the same time, as when the desired application material is one formed, just prior to application, upon interaction of the contents of the reservoirs 27 both reservoirs are compressed, by the application of pressure to the bottom walls 30 thereof causing their contents to enter said recesses 28 between which the materials are passed back & forth over said separation 27 to allow the reaction to proceed to the desired extent after which the distal ends of the applicator package are bent backwards towards each other, by pressure applied to the distal ends of the upper surface 13 of said backing member 2 whereby the slit or weakened portion 12 in the first member is caused to open permitting the desired application material to be absorbed by the pad 11 and then applied to said surface the bent back distal ends of the package or backing member, upon separation from the second member 3, serving as a handle for said pad 11.

Figure 9:
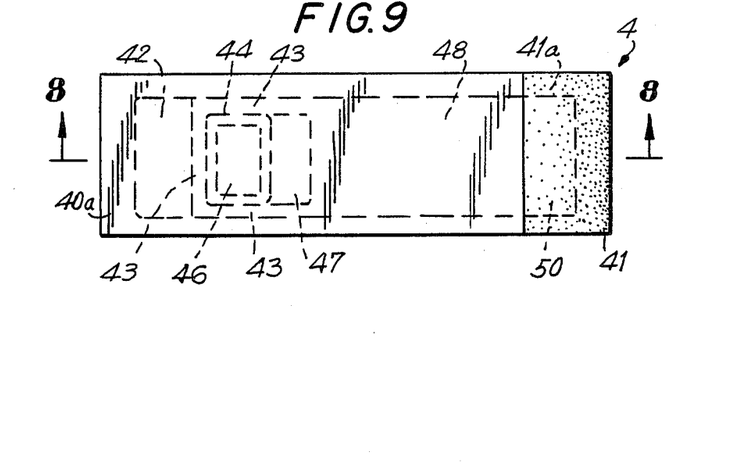
FIG. 9 is a top view of another embodiment of the invention.
Figure 10:
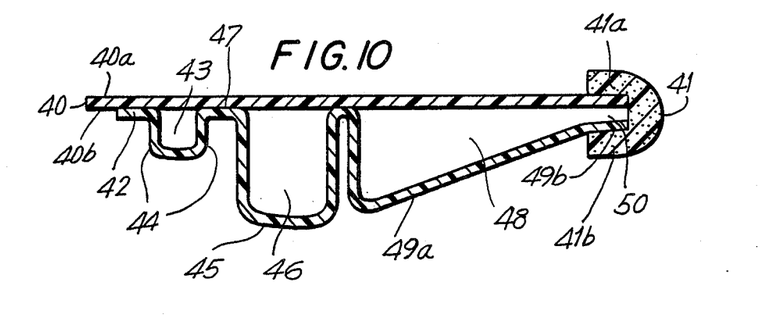
FIG. 10 is a sectional side view of said embodiment along line 8—8 of FIG. 9.

In FIGS. 9 and 10 there is illustrated another embodiment of this invention, designated by the numeral 4, comprising a backing member 40 to the top of the proximal end of which there is sealed a bent back portion 41b of an absorbent pad 41.

The underside 40b of said backing member is in sealable contact with a second member comprising a formed, flexible sheet comprising, at its distal end a cavity 46 to act as a reservoir for said flowable materials a second recess 48 tapered toward the proximal end of said member and terminating in a narrow space 50 adjacent said pad.

Said second member comprises a portion 42 thereof for sealing said second member to said backing member and forms the bottom 45 and side walls of the cavity 46.

A portion of said second member forms a separation 47 between, and is coplanar with the tops of, recesses 46 and 48 and forms the tapered side 49a and bottom walls of recess 48 the end 49b of said bottom wall being approximately horizontal, terminating at said pad 41 and spaced vertically from the underside of said backing member 40.

The remaining portion 41b of pad 40 is bent backward and sealed to the underside of bottom wall portion 49b.

The second member further comprises a groove 43 spaced horizontally, and separated by wall portion 44, from cavity 46.

Said cavity is separated from recess 48 by a portion 47 of said backing member in sealable cotact with said backing member and coplanar with the tops of recesses 46 and 48.

In the practice of using this embodiment of the invention slight pressure, as from a finger, is applied to the bottom wall 45 of cavity 46 causing said cavity to deform and the pressure to be transmitted through said flowable materials whereby the wall portion 44 and separation 47 are caused to delaminate. The flowable materials are then directed through grooves 43 and over the delaminated separation 47 into recess 48.

Further deforming pressure applied to the bottom wall 49a of cavity 48 causes the flowable materials to flow into space 50 and thence to the pad 41 from which it is dispensed as desired.

Continued pressure upon said wall 49a causes a continuous flow of said materials through said pad to the desired surfaces.

In this aspect of the invention the backing and second members, which are still in sealed contact with each other around their peripheral and distal edges, may be utilized as a handle for the absorbent pad.

The choice of materials, and methods, useful in preparation of the backing & second members for the practice of the invention, such as those described in U.S. Pat. No. 4,430,013, incorporated herein by reference, will depend upon the specific needs of the user as determined by the composition of the flowable materials and/or active materials contained within the reservoirs 27.

The instant invention having been described in detail with reference to the drawings is to be understood that various changes may be made in the described embodiments without departing from the scope of the invention as claimed.

What is claimed is:

1. An applicator package for the application of flowable materials to surfaces, comprising:
   (a) an applicator pad;
   (b) a backing member, one surface of which is in adhesive contact with said pad, comprising a first, flexible sheet;
   (c) a second member, in contact with the other surface of said backing member, comprising a formed semi-rigid sheet having at least one recess adjacent said pad; at least one cavity, or reservoir for flowable materials distally spaced from said recess; a peripheral groove in said second member whereby a tubular space is formed between said backing in fluid connection with said recess and spaced from the distal and side edges of said member and surrounding said cavity on its distal end and sides; coplanar separations, between said cavity and said groove and between said cavity and recess, in contact with said backing member, said backing member being sealed to said second member at the periphery thereof and at the separations between the cavity, groove and recess whereby pressure on the cavity portion of the second member causes at least one of said coplanar separations to separate from the backing member thereby allowing fluid to pass into the groove and then into said recess or, directly into the recess; and
   (d) a slit or weakened portion adjacent to said pad and between said pad and said recess to permit the flow of said flexible materials therethrough into said pad and therethrough to the desired surfaces.

2. The package of claim 1 wherein said backing member comprises said slit or weakened portion adjacent to said pad.

3. The package according to claim 1 wherein said second member comprises two cavities.

4. The package according to claim 1 wherein said second member comprises two recesses separated from each other by a separation, spaced below the plane of the co-planar separations of claim 1, providing fluid connection between said recesses.

5. The package according to claim 2 wherein said slit comprises a longitudinal slit.

6. The package according to claim 2 wherein said slit comprises a transverse slit.

7. The package according to claim 1 wherein said pad comprises a foamed material.

8. The package according to claim 1 wherein the adhesion between said first and second members is effected through heat sealing.

9. The package according to claim 1 wherein the adhesion between said backing and second members is effected by means of pressure-sensitive adhesives, with the proviso that said adhesives are not reactive with nor permeable to the contents of said reservoir.

10. The package according to claim 3 wherein within each of said cavities there is a different flowable material and the flowable materials contained in said cavities react with each other in said recess to form the material to be applied to said surface.

11. The package of claim 1 wherein said second member comprises a single cavity and a recess comprising tapered side walls the proximal end of the bottom wall of which is approximately parallel to, and spaced vertically from the absorbent pad which is situated adjacent to the proximal ends of said members and whose ends are bent backwards to adhesively contact the upper and lower sides of the backing and second members, respectively.

12. A disposable swab for the application of flowable materials to surfaces comprising an applicator package comprising:
(a) an applicator pad;
(b) a backing member, one surface of which is in adhesive contact with said pad, comprising a first, flexible sheet comprising a slit or weakened portion adjacent to said pad;
(c) a second member, in contact with the other surface of said backing member, comprising a formed semi-rigid sheet having at least one recess adjacent said slit or weakened portion, at least one cavity, or reservoir for flowable materials distally spaced from said recess; a peripheral groove in said second member whereby a tubular space is formed between said backing member and said second member. in fluid connection with said recess and spaced from the distal and side edges of said member and surrounding said cavity on its distal end and sides; co-planar separations, between said cavity and said groove and between said cavity and recess, in contact with said backing member, said backing member being sealed to said second member at the periphery thereof and at the separations between the cavity, groove and recess whereby pressure on the cavity portion of the second member causes at least one of said coplanar separations to separate from the backing member thereby allowing fluid to pass into the groove and then into said recess or, directly into the recess.

13. The swab according to claim 12 wherein said second member comprises two cavities.

14. The swab according to claim 12 wherein said second member comprises two recesses separated from each other by a separation, spaced below the plane of the co-planar separations of claim 12, providing fluid connection between said recesses.

15. The swab according to claim 12 wherein said slit comprises a longitudinal slit.

16. The swab according to claim 12 wherein said slit comprises a transverse slit.

17. The swab according to claim 12 wherein said pad comprises a foamed material.

18. The swab according to claim 12 wherein the adhesion between said first and second members is effected through heat sealing.

19. The swab according to claim 12 wherein the adhesion between said backing and second members is effected by means of pressure-sensitive adhesives, with the proviso that said adhesives are not reactive with nor permeable to the contents of said reservoir.

20. The swab according to claim 12 wherein within each of said cavities there is a different flowable material and the flowable materials contained in said cavities react with each other in said recess to form the material to be applied to said surface.

21. A method of applying flowable materials to surfaces comprising the steps of:
(a) applying pressure to the bottom wall of the cavity of an applicator package, for the application of flowable materials to surfaces, said package comprising
(1) an applicator pad;
(2) a backing member, one surface of which is in adhesive contact with said pad, comprising a first, flexible sheet comprising a slit or weakened portion adjacent to said pad;
(3) a second member, in contact with the other surface of said backing member, comprising a formed semi-rigid sheet having at least one recess adjacent said slit or weakened portion, at least one cavity, or reservoir for flowable materials distally spaced from said recess; a peripheral groove in said second member whereby a tubular space is formed between said backing member and said second member in fluid connection with said recess and spaced from the distal and side edges of said member and said groove and surrounding said cavity on its distal end and sides; co-planar separations, between said cavity and said groove and between said cavity and recess, in contact with said backing member, said backing member being sealed to said second member at the periphery thereof and at the separations between the cavity, groove and recess whereby pressure on the cavity portion of the second member causes at least one of said coplanar separations to separate from the backing member thereby allowing fluid to pass into the groove and then into said recess or, directly into the recess;
(b) opening said slit or rupturing and opening sadi weakened portion of said backing member by applying pressure to the distal ends of the backing member forcing the distal ends of said package backward around the transverse center of said backing member;
(c) forcing said flowable material into said pad through said opening by applying pressure to the bottom wall of said recess; and
(d) using said bent back ends as a handle for said pad, containing said flowable materials, to apply said flowable material to said surface.

22. The method of claim 21 wherein said second member comprises two cavities to the bottom wall of one or both of which pressure is applied as in step (a) of claim 21.

23. The method of claim 22 wherein said second member comprises two recesses separated from each other by a separation, spaced below the plane of the co-planar separations of claim 20, providing fluid connection between said recess and pressure is applied to the bottom wall of one or both of said cavities as in step (a) of claim 21 and subsequently to the bottom walls of said recesses and transfer of said flowable materials to said applicator pad.

24. The method of claim 23 wherein said cavities contain precursors to said flowable materials wherein prior to the transfer of said foamable materials to said applicator pad said precursors are caused to react by mixing in said recesses by transferrence therebetween over the separation therebetween until the desired extent of reaction has occurred.

25. The method of claim 21 wherein, after step (c), said backing and second members are separated and the distal ends of said backing member are bent backwards about the transverse central portion of said pad to form the handle of the swab comprising said backing member and pad.

* * * * *